(12) United States Patent
Galli et al.

(10) Patent No.: US 7,022,697 B2
(45) Date of Patent: Apr. 4, 2006

(54) 4-(OXADIAZOL-3-YL)-1,4-DIAZABICYCLO [3.2.2]-NONANE DERIVATIVES, PREPARATION AND THERAPEUTIC USE THEREOF

(75) Inventors: Frédéric Galli, Vaucresson (FR); Odile Leclerc, Massy (FR); Alistair Lochead, Charenton le Pont (FR)

(73) Assignee: Sanofi-aventis, Paris (FR)

( * ) Notice: Subject to any disclaimer, the term of this patent is extended or adjusted under 35 U.S.C. 154(b) by 14 days.

(21) Appl. No.: 10/495,891

(22) PCT Filed: Nov. 21, 2002

(86) PCT No.: PCT/FR02/03985

§ 371 (c)(1),
(2), (4) Date: May 18, 2004

(87) PCT Pub. No.: WO03/044019

PCT Pub. Date: May 30, 2003

(65) Prior Publication Data

US 2004/0266757 A1    Dec. 30, 2004

(30) Foreign Application Priority Data

Nov. 23, 2001    (FR) .................................. 01 15153

(51) Int. Cl.
*A61P 25/00* (2006.01)
*A61K 31/55* (2006.01)
*C07D 471/08* (2006.01)

(52) U.S. Cl. ........................ 514/219; 514/221; 540/556
(58) Field of Classification Search ................ 514/219, 514/221; 540/556
See application file for complete search history.

(56) References Cited

U.S. PATENT DOCUMENTS

| 5,478,939 A | 12/1995 | Trybulski et al. ............ 544/336 |
| 6,407,095 B1 | 6/2002 | Lochead et al. ............. 514/221 |
| 2003/0114461 A1 | 6/2003 | Galli et al. ................. 514/249 |

FOREIGN PATENT DOCUMENTS

| EP | 0307140 | 3/1989 |
| WO | WO 00/34279 | 6/2000 |
| WO | WO 01/92259 | 12/2001 |

*Primary Examiner*—Brenda Coleman
(74) *Attorney, Agent, or Firm*—Balaram Gupta

(57) ABSTRACT

The invention relates to compounds of the Formula I, to pharmaceutical compositions comprising them, and to the method of use thereof in the treatment or prevention of disorders linked to a dysfunction of the nicotinic receptors.

6 Claims, No Drawings

4-(OXADIAZOL-3-YL)-1,4-DIAZABICYCLO[3.2.2]-NONANE DERIVATIVES, PREPARATION AND THERAPEUTIC USE THEREOF

This application is a National Stage entry under 35 U.S.C. § 371 of International application No. PCT/FR02/03985 filed Nov. 21, 2002, which is incorporated herein by reference in its entirety.

The present invention relates to compounds which are ligands of nicotinic receptors and which are useful in the treatment or prevention of disorders linked to a dysfunction of the nicotinic receptors, especially within the central nervous system.

The compounds of the present invention correspond to the general formula (I)

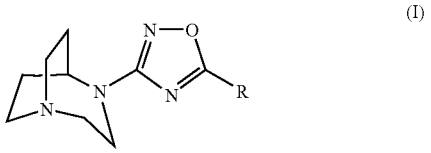

in which R represents a ($C_3$–$C_6$)cycloalkyl group or a phenyl group which is optionally substituted by one or more groups selected from a halogen atom, a ($C_1$–$C_6$)alkyl, ($C_1$–$C_6$)alkoxy, nitro, amino, di($C_1$–$C_3$)alkylamino, trifluoromethoxy, trifluoromethyl, cyano, hydroxyl or methylenedioxy group, or a piperid-1-yl or morpholin-4-yl or pyrrolidin-1-yl or azetidin-1-yl or azepin-1-yl or pyridyl or thienyl or pyrazinyl or furyl or benzofuryl or benzothienyl or indolyl or pyrimidinyl or piperazinyl or isoxazolyl or phenoxazinyl or dibenzofuryl or dibenzothienyl or pyrrolyl or naphthyl group, each of which groups may optionally be substituted by one or more groups selected from a halogen atom or a ($C_1$–$C_6$)alkyl, ($C_1$–$C_6$)alkoxy, trifluoromethoxy, trifluoromethyl, nitro, cyano, hydroxyl, amino, ($C_1$–$C_3$)dialkylamino or ($C_3$–$C_8$)cycloalkylamino group.

A subset of preferred compounds is that of the compounds of general formula (I) in which R represents a phenyl group which is optionally substituted by one or more halogen atoms or by one or more ($C_1$–$C_6$)alkyl, ($C_1$–$C_6$)alkoxy, nitro, amino, trifluoromethoxy, trifluoromethyl, cyano, hydroxyl or methylenedioxy groups, or a pyridyl group or a thienyl group.

The compounds of the invention can exist in the form of bases or of addition salts with acids.

The compounds of the invention may be prepared by a process which is illustrated by scheme 1 below.

1,4-Diazabicyclo[3.2.2]nonane of formula (II) is reacted with a compound of general formula (III) in which R is as defined above.

The reaction may be a nucleophilic substitution reaction performed in the presence of a strong base such as caesium carbonate or triethylamine. It is also possible to perform a Buchwald coupling reaction (J. Org. Chem. (1997), 62, 6066–6068) in the presence of a palladium catalyst such as palladium acetate or tris(dibenzylideneacetone)dipalladium (0), a complexing ligand such as triphenylphosphine, tributylphosphine or 2,2'-bis(diphenylphosphino)-1,1'-binaphthyl, and a base, for example an organic base such as sodium tert-butoxide or a mineral base such as caesium carbonate, or any other method of coupling.

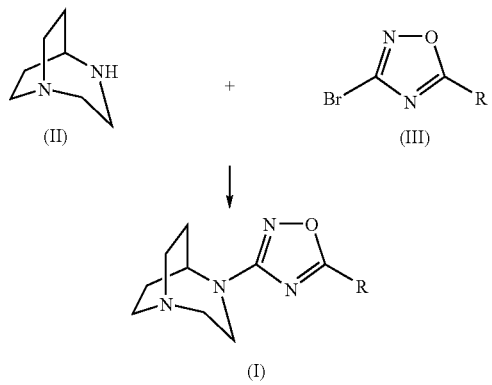

The preparation of 1,4-diazabicyclo-[3.2.2]nonane is described in J. Med. Chem. (1993), 36, 2311–2320.

The compounds of general formula (III) are obtainable from the corresponding nitrites and dibromoformaldoxime in accordance with a method described, for example, in J. Het. Chem. (1989), 26, 23. Dibromoformaldoxime is prepared by a method described, for example, in Tet. Lett. (1984), 487. Alternatively, the compounds of general formula (I) may be prepared in accordance with Scheme 2 below; 1,4-diazabicyclo[3.2.2]nonane of formula (II) is reacted with a compound of general formula (IV) in which R is as defined above. This gives an intermediate of general formula (V), which is finally cyclized in the presence of hydroxylamine.

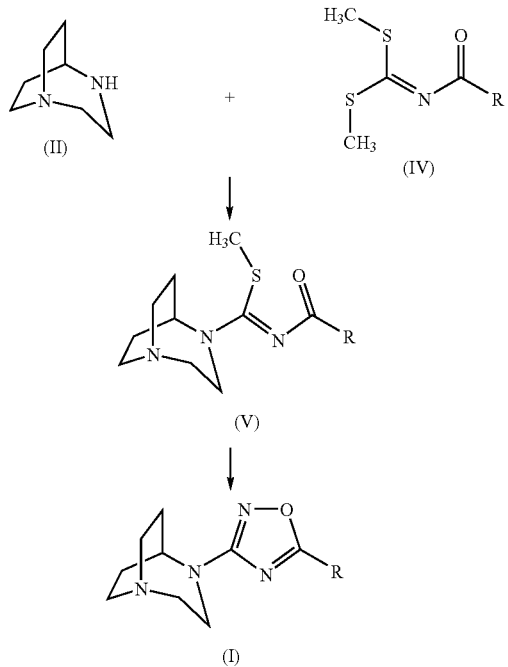

The compounds of general formula (IV) are obtainable by a method described, for example, in J. Het. Chem. (1990), 27, 1689.

The examples which follow illustrate the preparation of some compounds of the invention. The elemental microanalyses and the IR and NMR spectra, and also, in certain cases, the X-ray diffraction spectra, confirm the structures of the compounds obtained. The numbers indicated in brackets in the titles of the examples correspond to those of the 1$^{st}$ column of the table given later on below.

In the names of the compounds, the hyphen "-" forms part of the word and the underscore "_" serves only for the break at the end of a line; it should be omitted in the absence of a break and should be replaced neither by a normal hyphen nor by a space.

EXAMPLE 1

Compound No. 1

4-[5-Phenyl-(1,2,4-oxadiazol-3-yl)]-1,4-diazabicyclo[3.2.2]nonane hydrobromide 1:2

A 10 ml reactor is charged in succession with 0.2 g (1.6 mmol) of 1,4-diazabicyclo[3.2.2]nonane, 6 ml of tetrahydrofuran, 0.22 g (1.6 mmol) of 3-bromo-5-phenyl-(1,2,4) oxadiazole and 0.24 ml (1.7 mmol) of triethylamine and the mixture is heated at reflux for 20 hours.

It is poured into water, the aqueous phase is extracted with chloroform and the organic phases are dried, filtered and concentrated under reduced pressure. The residue is purified by chromatography on an alumina column, eluting with a 60/40 mixture of cyclohexane and ethyl acetate. This gives 0.11 g of product, which is dissolved in 20 ml of acetone, and then ml of a 33% strength solution of hydrobromic acid in acetic acid are added. The crystals obtained are recovered by filtration.

This gives 0.070 g of hydrobromide.
Melting point: 262–265° C.

EXAMPLE 2

Compound No. 9

4-(5-Thien-2-yl-[1,2,4]oxadiazol-3-yl)-1,4-diazabicyclo[3.2.2]nonane hydrobromide 2.1 N-[(1,4-Diazabicyclo[3.2.2]non-4-yl)(methyl_sulfanyl)methylene]thiophene-2-carboxamide. A 50 ml reactor is charged with 0.3 g (2.4 mmol) of 1,4-diazabicyclo[3.2.2]nonane, 10 ml of ethyl alcohol and 0.55 g (2.4 mmol) of N-[(bismethylsulfanyl)methylene]thiophene-2-carboxamide and the mixture is heated at reflux for 30 minutes and concentrated under reduced pressure.

This gives 0.74 g of an intermediate which is used without purification.

2.2 4-(5-Thien-2-yl-[1,2,4]oxadiazol-3-yl)-1,4-diazabicyclo[3.2.2]nonane hydrobromide A 100 ml reactor is charged with 0.74 g of N-[(1,4-diazabicyclo[3.2.2]non-4-yl)(methyl_sulfanyl)methylene] thiophene-2-carboxamide in solution in 20 ml of toluene and then 0.72 g (10.3 mmol) of hydroxylamine hydrochloride, 20 ml of ethyl alcohol and 20 ml of acetic acid are added and the mixture is heated at reflux for 1 hour. The solution is concentrated under reduced pressure and the residue is purified by chromatography on a silica gel column, eluting with a 95/5/0.5 mixture of chloroform, methanol and aqueous ammonia.

This gives 0.37 g of product, which is dissolved in 15 ml of acetone and then 0.25 ml of a 33% strength solution of hydrobromic acid in acetic acid is added and the crystals formed are recovered by filtration.

Melting point: 278–280° C.

The table below illustrates the chemical structures and physical properties of some compounds of the invention.

In the "Salt" column, "-" denotes a compound in the form of a base and "HBr" denotes a hydrobromide. The acid:base molar ratios are indicated opposite.

TABLE

| No. | R | Salt | m.p. ° C. |
|---|---|---|---|
| 1 | $C_6H_5$ | HBr 2:1 | 262–265 |
| 2 | 3-$CH_3$—$C_6H_4$ | HBr 1:1 | 271–272 |
| 3 | 2-F—$C_6H_4$ | HBr 1:1 | 275–276 |
| 4 | 3-$CF_3$—$C_6H_4$ | HBr 1:1 | 258–259 |
| 5 | 3-$OCH_3$—$C_6H_4$ | HBr 1:1 | 239–240 |
| 6 | 3-Cl—$C_6H_4$ | HBr 1:1 | 268–269 |
| 7 | 3-$OCF_3$—$C_6H_4$ | HBr 1:1 | 207–211 |
| 8 | pyrid-3-yl | HBr 1:1 | 260–264 |
| 9 | Thien-2-yl | HBr 1:1 | 278–280 |
| 10 | 3,4-($OCH_2O$)—$C_6H_3$ | HBr 1:1 | 266–272 |
| 11 | 4-$NH_2$—$C_6H_4$ | HBr 2:1 | 234–245 |
| 12 | 4-Br—$C_6H_4$ | HBr 1:1 | 276–278 |
| 13 | 3-$CH_3$-thien-2-yl | HBr 1:1 | 275–276 |
| 14 | pyrid-4-yl | HBr 1:1 | 269–272 |
| 15 | 4-$OCH_3$—$C_6H_4$ | HBr 1:1 | 274–275 |
| 16 | piperazin-2-yl | HBr 1:1 | 247–248 |
| 17 | 5-$CH_3$-2-$CF_3$-fur-3-yl | HBr 1:1 | 240–241 |
| 18 | 3-Br-thien-2-yl | HBr 1:1 | 245–250 |
| 19 | 4-$OCH_3$-thien-3-yl | HBr 1:1 | 278–280 |
| 20 | 6-$CH_3$-pyrid-3-yl | HBr 2:1 | 244–246 |
| 21 | naphth-1-yl | HBr 1:1 | 256–258 |
| 22 | 4-$CH_3$—$C_6H_4$ | HBr 1:1 | 269–271 |
| 23 | fur-2-yl | HBr 1:1 | 249–251 |
| 24 | benzothien-2-yl | HBr 1:1 | 258–260 |
| 25 | 5-$CF_3$-thien-2-yl | HBr 1:1 | 238–240 |
| 26 | 2-Cl-pyrid-4-yl | HBr 2:1 | 243–246 |
| 27 | 6-Cl-pyrid-3-yl | HBr 1:1 | 272–274 |
| 28 | 4-$NO_2$—$C_6H_4$ | HBr 1:1 | 279–281 |
| 29 | 2,4-$Cl_2$—$C_6H_3$ | HBr 1:1 | 266–268 |
| 30 | 3,4-$Cl_2$—$C_6H_3$ | HBr 1:1 | 269–271 |
| 31 | 3-$NO_2$—$C_6H_4$ | HBr 1:1 | 264–266 |
| 32 | 3-Cl-benzothien-2-yl | HBr 1:1 | 280–282 |

The compounds of the invention have been studied for their affinity for nicotinic receptors comprising the $\alpha_7$ subunit, according to the methods described by Mark and Collins in *J. Pharmacol. Exp. Ther.* 1982, 22, 564, and by Marks et al. in *Mol. Pharmacol.* 1986, 30, 427.

Male OFA rats weighing 150 to 200 g are decapitated and the entire brain is quickly removed, homogenized using a Polytron™ mill in 15 volumes of a 0.32M sucrose solution at 4° C. and then centrifuged at 1000 g for 10 min. The pellet is removed and the supernatant is centrifuged at 8000 g for 20 min at 4° C. The pellet is recovered and is homogenized using a Polytron™ mill in 15 volumes of double-distilled water at 4° C. and is then centrifuged at 8 000 g for 20 min. The pellet is removed and the supernatant and the layer of skin (buffy coat) are centrifuged at 40 000 g for 20 min. The pellet is recovered, is resuspended with 15 volumes of double-distilled water at 4° C. and is centrifuged a further time at 40 000 g for 20 min before being stored at −80° C.

On the day of the experiment, the tissue is slowly defrosted and is suspended in 5 volumes of buffer. 150 µl of this membrane suspension are preincubated at 37° C. for 30 min in darkness in the presence or in the absence of the test compound. The membranes are then incubated for 60 min at 37° C. in darkness in the presence of 50 µl of 1 nM [$^3$H]α-bungarotoxin in a final volume of 250 µl of HEPES 20 mM buffer. The reaction is halted by filtration through Whatman GF/C™ filters pretreated for 3 hours with 0.05% polyethyleneimine. The filters are rinsed with two times 5 ml of buffer at 4° C. and the radioactivity retained on each filter is measured by liquid scintigraphy. The non-specific binding in the presence of α-bungarotoxin at 1 µM final is determined; the non-specific binding represents approximately 60% of the total binding recovered on the filter. The percentage inhibition of the specific binding of [$^3$H]α-bungarotoxin is determined for each concentration of studied compound and then the $IC_{50}$, the concentration of compound which inhibits 50% of the specific binding, is calculated.

The $IC_{50}$ values of the most affinitive compounds of the invention lie between 0.007 and 0.30 µM.

The preceding results show that the compounds of the invention are selective ligands for $α_7$ subunits of the nicotinic receptor.

The results of the tests suggest the use of the compounds in the treatment or prevention of disorders linked to dysfunction of the nicotinic receptors, especially within the central nervous system.

These disorders comprise detrimental cognitive changes, more specifically detrimental memory changes, but also detrimental attentional changes, related to Alzheimer's disease, to pathological ageing (Age Associated Memory Impairment, AAMI), to Parkinsonian syndrome, to trisomy 21 (Down's syndrome), to Korsakoff's alcoholic syndrome or to vascular dementias (multi-infarct dementia, MID).

The compounds of the invention might also be of use in the treatment of motor disorders observed in Parkinson's disease or of other neurological diseases, such as Huntington's chorea, Tourette's syndrome, tardive dyskinesia and hyperkinesia.

The compounds of the invention may also constitute a curative or symptomatic treatment of acute neurodegenerative pathologies such as cerebral vascular accidents and cerebral hypoxic episodes, and also chronic neurodegenerative pathologies. They may be used in cases of psychiatric pathologies: schizophrenia, depression, anxiety, panic attacks or obsessive-compulsive behaviours.

They may prevent symptoms due to withdrawal from tobacco, from alcohol and from various dependency-inducing substances, such as cocaine, LSD, cannabis or benzodiazepines.

The present invention accordingly also provides pharmaceutical compositions comprising an effective dose of at least one compound according to the invention, in the form of a base or a pharmaceutically acceptable salt or solvate, as a mixture, if appropriate, with suitable excipients.

The said excipients are selected according to the pharmaceutical form and the method of administration desired.

The pharmaceutical compositions according to the invention may thus be intended for oral, sublingual, subcutaneous, intramuscular, intravenous, topical, intratracheal, intranasal, transdermal, rectal or intraocular administration.

The unit administration forms may be, for example, tablets, gelatin capsules, granules, powders, solutions or suspensions to be taken orally or to be injected, transdermal patches or suppositories. Ointments, lotions and collyria may be envisaged for topical administration.

The said unit forms are dosed to allow a daily administration of 0.01 to 20 mg of active principle per kg of body weight, according to the pharmaceutical dosage form.

To prepare tablets, a pharmaceutical vehicle, which can be composed of diluents, such as, for example, lactose, microcrystalline cellulose or starch, and formulation adjuvants, such as binders (polyvinylpyrrolidone, hydroxypropylmethylcellulose, etc.), flow agents, such as silica, and lubricants, such as magnesium stearate, stearic acid, glyceryl tribehenate or sodium stearylfumarate, is added to the micronized or unmicronized active principle. Wetting or surface-active agents, such as sodium lauryl sulphate, may also be added.

The preparation techniques may be direct tableting, dry granulation, wet granulation or hot melting.

The tablets can be uncoated, film-coated, for example with sucrose, or coated with various polymers or other appropriate materials. They can be designed to allow rapid, delayed or sustained release of the active principle by virtue of polymer matrices or of specific polymers used in the coating.

To prepare gelatin capsules, the active principle is mixed with dry pharmaceutical vehicles (simple mixing, dry or wet granulation, or hot melting) or liquid or semi-solid pharmaceutical vehicles.

The gelatin capsules can be hard or soft and can be uncoated or coated with a thin film, so as to have a rapid, sustained or delayed activity (for example, for an enteric form).

A composition in the form of a syrup or an elixir or for administration in the form of drops may comprise the active principle in conjunction with a sweetener, preferably a calorie-free sweetener, methylparaben or propylparaben as antiseptic, a flavour enhancer and a colourant.

The water-dispersible powders and granules may comprise the active principle as a mixture with dispersing agents or wetting agents, or dispersants such as polyvinylpyrrolidone, as well as with sweeteners and taste corrigents.

Recourse is had, for rectal administration, to suppositories prepared with binders which melt at the rectal temperature, for example cocoa butter or polyethylene glycols.

Use is made, for parenteral administration, of aqueous suspensions, isotonic saline solutions or injectable sterile solutions comprising pharmacologically compatible dispersing and/or wetting agents, for example propylene glycol or butylene glycol.

The active principle may also be formulated in the form of microcapsules, optionally with one or more vehicles or additives, or else with a polymer matrix or with a cyclodextrin (transdermal patches or sustained release forms).

The topical compositions according to the invention comprise a medium compatible with the skin. They may be provided in particular in the form of aqueous, alcoholic or aqueous/alcoholic solutions, of gels, of water-in-oil or oil-in-water emulsions having the appearance of a cream or gel, of microemulsions or of aerosols or else in the form of vesicular dispersions comprising ionic and/or nonionic lipids. These pharmaceutical dosage forms are prepared according to methods conventional in the fields under consideration.

Finally, the pharmaceutical compositions according to the invention may comprise, in addition to a compound of general formula (I), other active principles which may be of use in the treatment of the disorders and diseases indicated above.

The invention claimed is:
1. A compound of the formula (I)

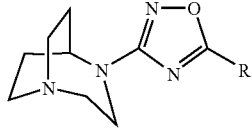

in which R represents a $(C_3–C_6)$cycloalkyl group or a phenyl group which is optionally substituted by one or more groups selected from a halogen atom, a $(C_1–C_6)$ alkyl, $(C_1–C_6)$ alkoxy, nitro, amino, di$(C_1–C_3)$alkylamino, trifluoromethoxy, trifluoromethyl, cyano, hydroxyl or methylenedioxy group, or a piperid-1-yl or 4-morpholinyl or pyrrolidin-1-yl or azetidin-1-yl or azepin-1-yl or pyridyl or piperazinyl or thienyl or pyrazinyl or furyl or benzofuryl or benzothienyl or indolyl or pyrimidinyl or isoxazolyl or phenoxazinyl or dibenzofuryl or dibenzothienyl or pyrrolyl or naphthyl group, each of which groups may optionally be substituted by one or more groups selected from a halogen atom or a $(C_1–C_6)$alkyl, $(C_1–C_6)$alkoxy, trifluoromethoxy, trifluoromethyl, nitro, cyano, hydroxyl, amino, $(C_1–C_3)$dialkylamino or $(C_3–C_8)$cycloalkylamino group, in the form of a base or an addition salt with an acid.

2. The compound according to claim 1, wherein R represents a phenyl group which is optionally substituted by one or more halogen atoms or by one or more $(C_1–C_6)$alkyl, $(C_1–C_6)$alkoxy, nitro, amino, trifluoromethoxy, trifluoromethyl, cyano, hydroxyl or methylenedioxy groups, or a pyridyl group or a thienyl group.

3. A method for the treatment of a disease selected from the group consisting of schizophrenia, Alzheimer's disease, Parkinson's disease, Down's syndrome, Korsakoff's alcoholic syndrome, vascular dementia, depression, anxiety, panic attack and obsessive-compulsive behavior, which comprises administering to a patient in need of such treatment an effective amount of a compound according to claim 1.

4. A pharmaceutical composition comprising a compound according to claim 1 in combination with an excipient.

5. A method for the treatment of a disease selected from the group consisting of schizophrenia, Alzheimer's disease, Parkinson's disease, Down's syndrome, Korsakoff's alcoholic syndrome, vascular dementia, depression, anxiety, panic attack and obsessive-compulsive behavior, which comprises administering to a patient in need of such treatment an effective amount of a compound according to claim 2.

6. A pharmaceutical composition that comprises a compound according to claim 2 in combination with an excipient.

* * * * *